US00PP15332P2

(12) United States Plant Patent
Stewart

(10) Patent No.: US PP15,332 P2
(45) Date of Patent: Nov. 16, 2004

(54) ***ANIGOZANTHOS* PLANT NAMED 'BUSH INFERNO'**

(50) Latin Name: *Anigozanthos flavidus*
Varietal Denomination: Bush Inferno

(75) Inventor: Angus Stewart, Erina (AU)

(73) Assignee: Ramm Botanicals Pty. Ltd., Tuggerah (AU)

( * ) Notice: Subject to any disclaimer, the term of this patent is extended or adjusted under 35 U.S.C. 154(b) by 0 days.

(21) Appl. No.: 10/747,788

(22) Filed: Dec. 29, 2003

(51) Int. Cl.[7] ..... A01H 5/00
(52) U.S. Cl. ..... Plt./362
(58) Field of Search ..... Plt./362

*Primary Examiner*—Anne Marie Grunberg
*Assistant Examiner*—June Hwu
(74) *Attorney, Agent, or Firm*—C. A. Whealy

(57) ABSTRACT

A new and distinct cultivar of *Anigozanthos* plant named 'Bush Inferno', characterized by its compact and upright plant habit; moderately vigorous growth habit; freely and continuous flowering habit; branched flowering stems; and bright orange-colored flowers.

1 Drawing Sheet

Botanical classification/cultivar designation: *Anigozanthos flavidus* cultivar Bush Inferno.

BACKGROUND OF THE INVENTION

The present Invention relates to a new and distinct cultivar of *Anigozanthos* plant, commonly referred to as Kangaroo-Paw, botanically known as *Anigozanthos flavidus*, and hereinafter referred to by the cultivar name Bush Inferno.

The new *Anigozanthos* is a product of a planned breeding program conducted by the Inventor in Tuggerah, New South Wales, Australia. The objective of the program is to create new compact *Anigozanthos* cultivars that have a long flowering period, branched flowering stems, bright flower coloration and improved disease resistance.

The new *Anigozanthos* originated from a cross-pollination made by the Inventor of the *Anigozanthos flavidus* cultivar Joey Calypso, not patented, as the female, or seed, parent with an unidentified selection of *Anigozanthos flavidus*, not patented, as the male, or pollen, parent. The new *Anigozanthos* was discovered and selected by the Inventor in a controlled environment in Tuggerah, New South Wales, Australia, on Aug. 10, 1998 from the resultant progeny of the above-mentioned cross-pollination.

Asexual reproduction of the new cultivar by in vitro propagation of micro-plants since February, 1999 in Tuggerah, New South Wales, Australia, has shown that the unique features of this new *Anigozanthos* are stable and reproduced true to type in successive generations.

SUMMARY OF THE INVENTION

Plants of the cultivar Bush Inferno have not been observed under all possible environmental conditions. The phenotype may vary somewhat with variations in environment such as temperature and light intensity, without, however, any variance in genotype.

The following traits have been repeatedly observed and are determined to be the unique characteristics of 'Bush Inferno'. These characteristics in combination distinguish 'Bush Inferno' as a new and distinct cultivar of *Anigozanthos:*

1. Compact and upright plant habit.
2. Moderately vigorous growth habit.
3. Freely and continuous flowering habit.
4. Freely branched flowering stems.
5. Bright orange-colored flowers.

Plants of the cultivar Bush Inferno can be compared to plants of the female parent, the cultivar Joey Calypso. In side-by-side comparisons conducted by the Inventor in Tuggerah, New South Wales, Australia, plants of the new *Anigozanthos* and the cultivar Joey Calypso differed in the following characteristics:

1. Plants of the new *Anigozanthos* had dark green-colored foliage whereas plants of the cultivar Joey Calypso had greyed green-colored foliage.
2. Plants of the new *Anigozanthos* had branched flowering stems whereas plants of the cultivar Joey Calypso did not have branched flowering stems.
3. Plants of the new *Anigozanthos* had bright orange-colored flowers whereas plants of the cultivar Joey Calypso had yellow orange-colored flowers.

Plants of the cultivar Bush Inferno can be compared to plants of the male parent, the unidentified selection of *Anigozanthos flavidus.* In side-by-side comparisons conducted by the Inventor in Tuggerah, New South Wales, Australia, plants of the new *Anigozanthos* and the male parent selection differed in the following characteristics:

1. Plants of the new *Anigozanthos* had curved leaves whereas plants of the male parent selection had straight leaves.
2. Plants of the new *Anigozanthos* had shorter leaves than plants of the male parent selection.
3. Plants of the new *Anigozanthos* had shorter flowering stems than plants of the male parent selection.

Plants of the new *Anigozanthos* can be compared to plants of the cultivar Bush Spark, disclosed in a U.S. Plant patent application Ser. No. 10/747,787 filed concurrently. In side-by-side comparisons conducted in Lompoc, Calif., plants of the new *Anigozanthos* differed from plants of the cultivar Bush Spark in the following characteristics:

1. Flowering stems of plants of the new *Anigozanthos* were not as freely branching as flowering stems of plants of the cultivar Bush Spark.
2. Plants of the new *Anigozanthos* had larger flowers and inflorescences than plants of the cultivar Bush Spark.
3. Plants of the new *Anigozanthos* had bright orange-colored flowers whereas plants of the cultivar Bush Spark had bright red to red purple-colored flowers.

Plants of the cultivar Bush Inferno can also be compared to plants of the cultivar Bush Ranger, disclosed in U.S. Plant Pat. No. 6,478. In side-by-side comparisons conducted by the Inventor in Tuggerah, New South Wales, Australia, plants of the new *Anigozanthos* and the cultivar Bush Ranger differed in the following characteristics:

1. Plants of the new *Anigozanthos* had curved leaves whereas plants of the cultivar Bush Ranger had straight leaves.
2. Plants of the new *Anigozanthos* had bright orange-colored flowers whereas plants of the cultivar Bush Ranger had red-colored flowers.

Plants of the cultivar Bush Inferno can also be compared to plants of the cultivar Bush Garnet, not patented. In side-by-side comparisons conducted by the Inventor in Tuggerah, New South Wales, Australia, plants of the new *Anigozanthos* and the cultivar Bush Garnet differed in the following characteristics:

1. Plants of the new *Anigozanthos* had curved leaves whereas plants of the cultivar Bush Garnet had slightly curved leaves.
2. Plants of the new *Anigozanthos* flowered earlier than plants of the cultivar Bush Garnet.
3. Plants of the new *Anigozanthos* had bright orange-colored flowers whereas plants of the cultivar Bush Garnet had dark red-colored flowers.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Anigozanthos*.

The photograph at the top of the sheet comprises a side perspective view of typical flowering plant of 'Bush Inferno' grown in a container.

The photograph at the bottom of the sheet is a close-up view of typical flowers of 'Bush Inferno'.

DETAILED BOTANICAL DESCRIPTION

Plants used in the aforementioned photographs and following description were grown under greenhouse conditions which closely approximate commercial production conditions during the winter and spring in Lompoc, Calif. Rooted young plants were grown in one-gallon containers in a polycarbonate-covered greenhouse and were about 17 weeks from planting when the photographs and description were taken. During the production of the plants, day temperatures ranged from 18 to 24° C., night temperatures ranged from 16 to 18° C. and light levels ranged from 4,000 to 8,000 foot-candles. In the following description, color references are made to The Royal Horticultural Society Colour Chart, 1995 Edition, except where general terms of ordinary dictionary significance are used.

Botanical classification: *Anigozanthos flavidus* cultivar Bush Inferno.

Parentage:

*Female, or seed, parent.*—*Anigozanthos flavidus* cultivar Joey Calypso, not patented.

*Male, or pollen, parent.*—Unidentified selection of *Anigozanthos flavidus,* not patented.

Propagation:

*Type cutting.*—In vitro propagation of micro-plants.

*Time to initiate roots, summer and winter.*—About 7 days at 23° C.

*Time to produce a rooted young plant, summer.*—About 42 days at 25° C.

*Time to produce a rooted young plant, summer.*—About 56 days at 25° C.

*Root description.*—Fibrous, freely branching and white in color.

Plant description:

*Form.*—Upright and compact plant habit with branched flowering stems with bright orange-colored flowers. Leaves in tight clumps; leaves curved downwards. Freely clumping and short internodes, full and dense plants. Moderately vigorous growth habit.

*Plant height* (*soil level to top of leaves*).—About 36 cm.

*Plant height* (*soil level to top of flowers*).—About 47 cm.

*Plant diameter.*—About 48 cm.

*Lateral branch description.*—Length: About 3 cm. Diameter: About 7 mm. Internode length: About 5 mm. Texture: Smooth, glabrous. Color: 145A.

*Foliage description.*—Arrangement: Alternate, equitant, simple; sessile. Length: About 34 cm. Width: About 3 cm. Shape: Ensiform; folded at base. Apex: Acute. Base: Clasping. Margin: Entire. Texture, upper and lower surfaces: Smooth, glabrous; thick, leathery. Venation pattern: Parallel. Color: Developing foliage, upper surface: 145B. Developing foliage, lower surface: 147A. Fully developed foliage, upper and lower surfaces: 147A. Venation, upper surface: 147D. Venation, lower surface: 147A.

Flower description:

*Flower type and flowering habit.*—Large flowers arranged singly on terminal and axillary racemes. Flowering stems freely branching. Flowers held initially upright then curving outward and eventually reflex with development. Flowers persistent. Freely and continuous flowering habit; about 25 flowers per inflorescence and potentially about 150 flowers and flower buds per flowering stem. Flowers not fragrant.

*Flower shape.*—Tubular perianth; zygomorphic.

*Natural flowering season.*—Plants flower throughout the summer in Southern California.

*Flower longevity on the plant.*—About 25 to 30 days.

*Inflorescence height.*—About 15 cm.

*Inflorescence diameter.*—About 4 to 4.5 cm.

*Flower height.*—About 3.7 cm.

*Flower diameter.*—About 5 to 6 mm.

*Flower buds.*—Length: About 2.5 cm. Diameter: About 4 to 6 mm. Shape: Tubular, curved. Texture: Tomentose. Color: 14A; tomentum, 34A to 34B.

*Perianth.*—Shape: Fused elongated tube with six reflexed acute petal apices; split on lower side. Perianth length: About 3.7 cm. Perianth diameter: About 4 to 6 mm. Petal apex length: About 1 cm. Petal apex width: About 2.5 mm. Texture, outside: Tomentose. Texture, inside: Smooth, glabrous. Color: Developing and fully developed flowers, outside surface: 151A; tomentum, 34A to 34B; tomentum becoming closer to 31C in color with development. Developing and fully developed flowers, inside surface: 144B.

*Floral bracts.*—Length: About 1.1 cm. Width: About 3 mm. Shape: Ensiform. Apex: Sharply acute. Base: Clasping. Texture, upper and lower surfaces: Tomentose. Color, upper and lower surfaces: Close to 147B; tomentum, 45C.

*Peduncles* (*flowering stems*).—Length: About 40 cm. Diameter: About 7 mm. Strength: Strong, stout. Angle: Upright but bending with weight of developed inflorescences to about 45° from vertical. Texture: Tomentose. Color: 147B; tomentum, 156B.

*Pedicels.*—Length: About 5 mm. Diameter: About 2 mm. Strength: Strong. Angle: Initially appressed to flowering stems, with development, about 90° from flowering stems. Texture: Tomentose. Color: 14A; tomentum, 34A to 34B.

*Reproductive organs.*—Stamens: Quantity per flower: About six. Anther length: About 2 mm. Anther diameter: About 1 mm. Anther shape: Oblong. Anther color: 13C. Pollen amount: Scarce. Pollen color: 13C. Pistils: Quantity per flower: One. Pistil length: About 3.5 cm. Stigma shape: Globose. Stigma color: 144A. Style length: About 3 cm. Style color: 151A. Ovary color: 143C.

*Seed/fruit.*—Seed and fruit production have not been observed.

Disease/pest resistance: Plants of the new *Anigozanthos* have been noted to be relatively resistant to Alternaria spp. Plants of the new *Anigozanthos* have not been observed to be resistant to other pathogens and pests common to *Anigozanthos.*

Weather tolerance: Plants of the new *Anigozanthos* have exhibited good tolerance to rain and wind and to tolerate temperatures from 1 to about 40° C.

It is claimed:

1. A new and distinct cultivar of *Anigozanthos* plant named 'Bush Inferno', as illustrated and described.

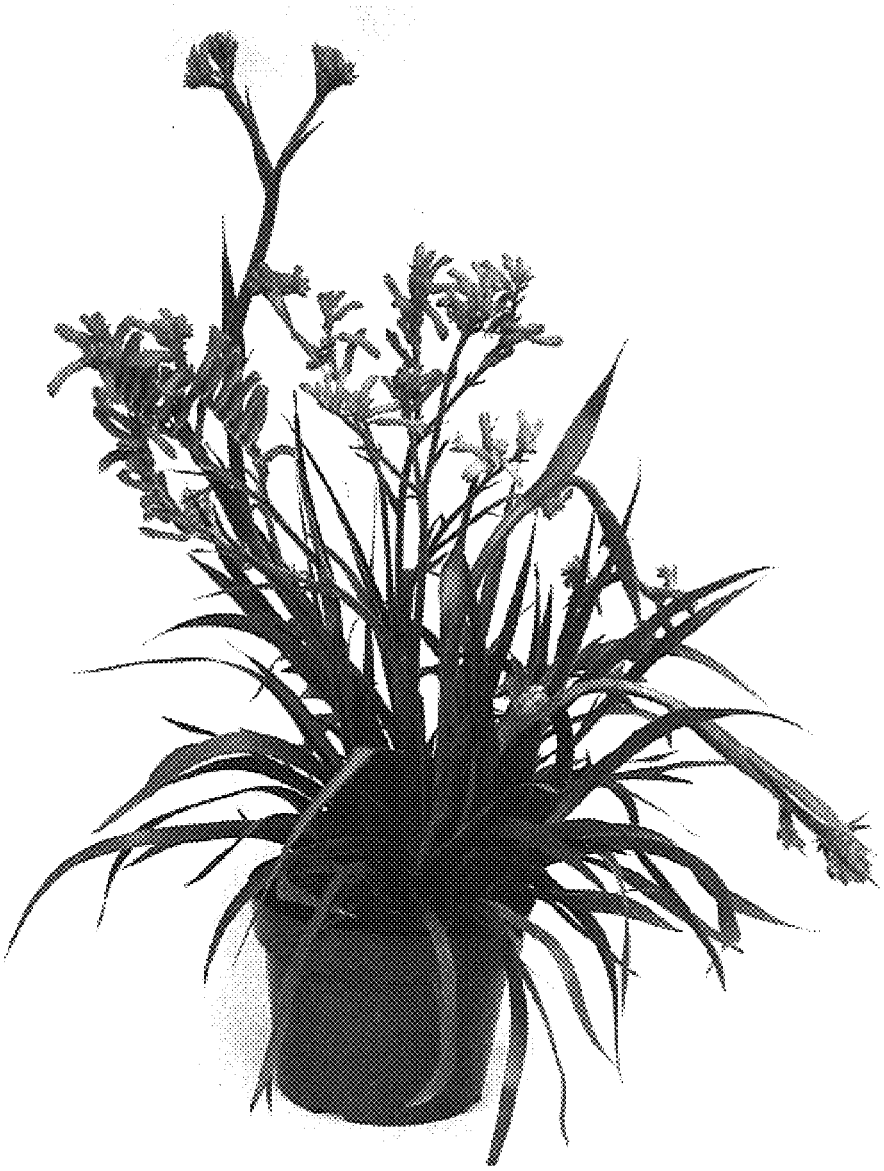
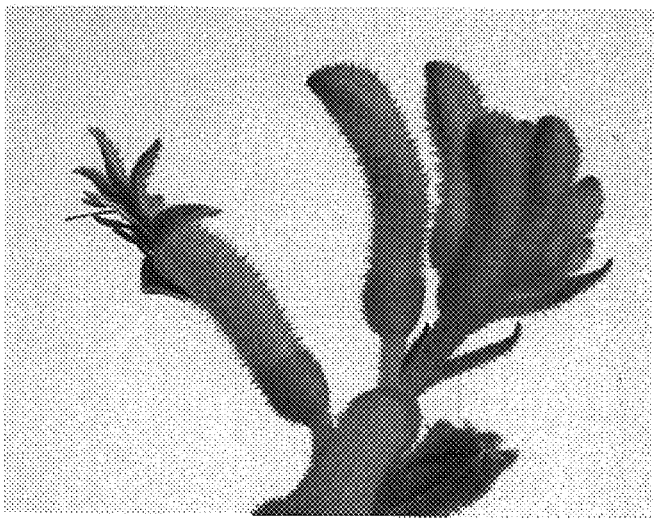

* * * * *